US005679784A

United States Patent [19]
Ladant et al.

[11] Patent Number: 5,679,784
[45] Date of Patent: Oct. 21, 1997

[54] RECOMBINANT MUTANTS FOR INDUCING SPECIFIC IMMUNE RESPONSES

[75] Inventors: Daniel Ladant, Cachan; Claude Leclerc, Paris; Peter Sebo, Paris; Agnes Ullmann, Paris, all of France

[73] Assignee: Institut Pasteur, Paris, France

[21] Appl. No.: 479,400

[22] Filed: Jun. 7, 1995

Related U.S. Application Data

[62] Division of Ser. No. 336,087, Nov. 7, 1994, which is a continuation of Ser. No. 11,644, Jan. 29, 1993, abandoned, which is a continuation-in-part of Ser. No. 871,795, Apr. 21, 1992, abandoned.

[51] Int. Cl.$^6$ .......................... C07H 21/04; A61K 39/00
[52] U.S. Cl. .................. 536/23.7; 424/184.1; 424/240.1; 435/320.1; 435/252.3; 435/69.3
[58] Field of Search .................. 536/23.7; 435/320.1, 435/69.3, 252.3; 424/184.1, 240.1

[56] References Cited

U.S. PATENT DOCUMENTS

| | | |
|---|---|---|
| 5,182,211 | 1/1993 | Girard et al. |
| 5,183,745 | 2/1993 | Danchin et al. |
| 5,312,902 | 5/1994 | Montagnier et al. |

FOREIGN PATENT DOCUMENTS

| | | |
|---|---|---|
| 0 406 857 A1 | 1/1991 | European Pat. Off. |
| WO 92/00099 | 1/1992 | WIPO |

OTHER PUBLICATIONS

Goyard et al., Bordetella pertussis Adenylate Cyclase: A Toxin with Multiple Talents, Zbl. Bakt. 278, 326–333 (1993).
Epitopes of HIV and SIV. I. Host Responses; AIDS Res Human Retroviruses, 7(2) :144–147 (1991). [Entire Section, pp. 144–147.].
Aichele et al., Antiviral Cytotoxic T Cell Response Induced by In Vivo Priming with a Free Synthetic Peptide, J. Exp. Med. 171(5): 1815–1820 (1990).
Glaser et al., Identification of residues essential for catalysis and binding of calmodulin in Bordetella pertussis adenylate cyclase by site–directed mutagenesis, EMBO Journal 8(3):967–972 (1989).
Ladant et al., Insertional Mutagenesis of Bordetella pertussis Adenylate Cyclase, J. Biol. Chem., 267(4):2244–2250 (1992).
Leclerc et al., The Cellular Location of a Foreign B Cell Epitope Expressed By Recombinant Bacteria Determines Its T Cell–Independent or T Cell–Dependent Characteristics, J. Immunol., 147:3542–3552 (1991).
Fayolle et al., In Vivo Induction of Cytotoxic T Cell Response by a Free Synthetic Peptide Requires CD4$^+$ T Cell Help, J. Immunol., 147: 4069–4073 (1991).
Leclerc et al., Identification of a T–Cell Epitope Adjacent to Neutralization Antigenic Site 1 of Poliovirus Type 1, J. Virol., 65(2) :711–718 (1991).

Sebo et al., High–level synthesis of active adenylate cyclase toxin of Bordetella pertussis in a reconstructed Escherichia coli system, Gene, 104:19–24 (1991).
Hanski, Invasive adenylate cyclase toxin of Bordetella pertussis, TIBS 14:459–463 (1989).
Moore et al., Introduction of Soluble Protein into the Class I Pathway of Antigen Processing and Presentation, Cell 54:777–785 (1988).
Schulz et al., Major histocompatibility complex–dependent T cell epitopes of lymphocytic choriomeningitis virus nucleoprotein and their protective capacity against viral disease, Eur. J. Immunol. 19:1657–1667 (1989).
Tam et al., Vaccine engineering: Enhancement of immunogenecity of synthetic peptide vaccines related to hepatitis in chemically defined models consisting of T– and B–cell epitopes, Proc. Nat'l Acad. Sci. USA 86:9084–9088 (1989).
Cassell et al., Linked Recognition of Helper and Cytotoxic Antigenic Determinants for the Generation of Cytotoxic T Lymphocytes, Ann. N.Y. Acad. Sci. 51–60 (1991).
Method for introducing a peptide into the cytosol; by linking to a toxin to translocate the peptide to the cytosol and presentation at the cell surface as a Class I MHC antigen; recombinant vaccine preparation, Vaccine, vol. 10, p. 638 (1992).
Welch, MicroReview: Pore–forming cytolysins of Gram–negative bacteria, Mol. Microbiol. 5(3):521–528 (1991).
Bowie et al., Deciphering the Message in Protein Sequences: Tolerance to Amino Acid Substitutions, Science 247:1306–1310 (1990).
Forestier et al., Identification of RTX Toxin Target Cell Specificity Domains by Use of Hybrid Genes, Infect. & Immun. 59(11):4212–4220 (1991).
Hart et al., Priming of anti–human immunodeficiency virus (HIV) CD8$^+$ cytotoxic T cells in vivo by carrier–free HIV synthetic peptides, Proc. Natl. Acad. Sci. USA 88:9448–9452 (1991).
Norley et al., Vaccination against HIV, Immunobiol. 184:193–207 (1992).
Goyard et al., Analysis of Bordetella pertussis cya operon regulation by use of cya–lac fusions, FEMS Microbiol. Lett. 77:251–256 (1991).

Primary Examiner—Paula K. Hutzell
Assistant Examiner—Benet Prickril
Attorney, Agent, or Firm—Finnegan, Henderson, Farabow, Garrett and Dunner, L.L.P.

[57] ABSTRACT

A recombinant plasmid comprises the cyaC and the cyaA genes of Bordetella which directs the expression of Bordetella, adenylate cyclase in a transformed host cell. A recombinant DNA molecule can comprise the Bordetella cyaA gene containing at least one insertion of a heterologous DNA sequence at at least one permissive site. In addition, a recombinant Bordetella adenylate cyclase comprises a heterologous epitope at a permissive site. Methods of inducing a specific B cell, helper T cell, and CTL cell immune response are provided.

10 Claims, 1 Drawing Sheet

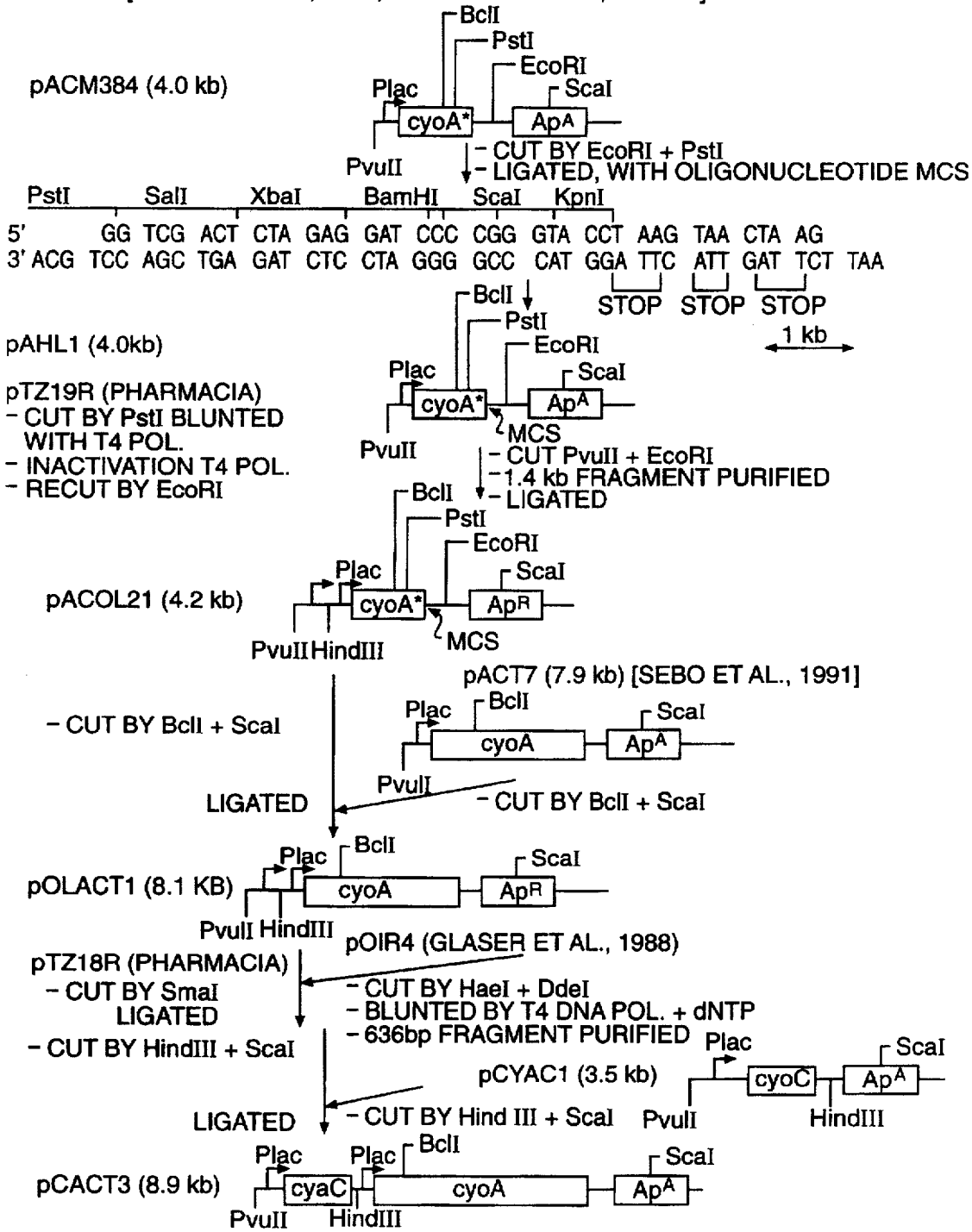

RECOMBINANT MUTANTS FOR INDUCING SPECIFIC IMMUNE RESPONSES

CROSS-REFERENCE TO RELATED APPLICATION

This is a division of application Ser. No. 08/336,087, filed Nov. 7, 1994 which is a continuation of application Ser. No. 08/011,644 filed Jan. 29, 1993 (now abandoned), which is a continuation-in-part of application Ser. No. 07/871,795 filed Apr. 21, 1992 now abandoned.

BACKGROUND OF THE INVENTION

This invention relates to a recombinant DNA molecule comprising the adenylate cyclase toxin gene (cyaA) or a fragment thereof containing an insertion of a heterologous DNA sequence at a permissive site, wherein the fragment encodes a polypeptide exhibiting the same immunological properties as the CyaA gene product. In specific embodiments of this invention the heterologous DNA sequence encodes an immunological epitope. CyaA can be obtained from any microorganism or otherwise.

This invention also relates to a recombinant adenylate cyclase comprising a heterologous epitope at a permissive site. In specific embodiments of this invention the heterologous epitope is inserted in the N-terminal catalytic domain of the recombinant adenylate cyclase and can be presented to the immune system in association with class I major histocompatability complex (MHC). In other embodiments of this invention the heterologous epitope is inserted in the C-terminal catalytic domain and can be presented to the immune system in association with class II MHC.

This invention further relates to methods of inducing specific immune responses in animals immunized with immunological compositions comprising recombinant adenylate cyclases. In specific embodiments of this invention B cell, CD4$^+$, and cytotoxic T cell responses are specifically induced.

With the advent of recombinant DNA techniques for modifying protein sequences, considerable work has been directed toward specifically altering or improving existing proteins. Modification of specific amino acids of enzymes of known structure to alter specificity has been achieved by site-directed mutagenesis. Although knowledge of the three-dimensional structure is restricted to a limited number of proteins, sequence comparisons between members of families of homologous proteins, as well as increasingly accurate predictions of secondary and tertiary structures, offer a useful basis for redesigning enzyme function.

Another approach of great potential interest is the insertion of new peptide sequences within a defined protein. Insertional mutagenesis has been efficiently used to study the topology of membrane proteins (Charbit et al., 1986, 1991) and, in the case of soluble proteins, to determine regions of natural flexibility (Barany, 1985a, 1985b; Freimuth and Ginseberg, 1986; Starzyk et al., 1989; Freimuth et al., 1990; Kumar and Black, 1991). Besides, insertion of a specific exogenous peptide within an enzyme could alter its catalytic or regulatory properties, thus providing a rational basis for protein engineering. Additionally, protein engineering can be used to alter or specifically direct the immune response to a defined epitope by altering the environment of the epitope.

The immune response can be divided into two distinct systems, cellular immunity and humoral immunity. Humoral immunity is mediated by soluble molecules, principally antibodies. In contrast, cellular immunity is mediated by intact cells, mostly T lymphocytes. The exact immune response generated by a foreign antigen is dependent on the nature of the antigen and the environment in which the antigen or an epitope of the antigen is presented to the immune system.

The initiating event in a humoral immune response is the binding of a B epitope to a membrane associated immunoglobulin (Ig) on a specific subset of B cells. This binding stimulates the entry of the B cells into the cell cycle, eventually resulting in the production of antibodies specifically recognizing the B epitope. The antibody response elicited by a B epitope can be T cell-dependent or T cell-independent. T cell-dependent responses are characterized by a very low primary response followed by an IgG memory response. The T cell-independent response, on the other hand, is characterized by a rapid, intense and prolonged IgM antibody response.

The cell mediated immune response is activated by T epitopes. T epitopes generally fall into two categories. Many epitopes can activate both T cells and B cells and are thus both T epitopes and B epitopes. Other T epitopes are denatured forms of native antigenic determinants and cannot activate a B cell mediated humoral immune response.

To activate a cell mediated immune response the T epitope must become associated with molecules of the major histocompatability complex (MHC). The MHC is a region of highly polymorphic genes whose products are expressed on the surface of various cells. There are two principle groups of MHC. Class I MHC is a transmembrane protein comprised of two polypeptide chains. The molecule contains an extracellular peptide binding region that is polymorphic at the peptide binding site, an immunoglobulin region, a transmembrane region, and a cytoplasmic domain that contains phosphorylation sites for a cAMP dependent protein kinase.

Class I MHC is found on virtually all nucleated cells. Class I MHC generally associate with endogenously synthesized T epitopes for presentation to the cell mediated immune system. As this association of class I MHC to specific antigen occurs in the endoplasmic reticulum, antigens that are internalized by an antigen presenting cell via the endocytotic pathway will generally not become associated with class I MHC. The association of a specific T epitope with class I MHC and incorporation of the antigen-MHC class I complex on the surface of a cell stimulates specific cytotoxic T lymphocytes (CTL). The stimulated cytotoxic T lymphocytes can then kill the cell expressing the antigen-MHC complex by granule exocytosis of a membrane pore forming protein that causes cell lysis and secretion of a cell toxin that activates DNA degrading enzymes. However, the activation of the CTL cells also requires the activation of T helper cells in certain cases.

The other major class of MHC proteins is class II MHC. Class II MHC are also transmembrane proteins. Like class I MHC, class II MHC comprises two polypeptide chains and includes a polymorphic peptide binding region, an immunoglobulin-like region, a transmembrane region and a cytoplasmic domain. However, unlike class I MHC, class II molecules are only expressed on "antigen presenting cells" such as B-lymphocytes, macrophages, dendritic cells, endothelial cells, and a few others. T-epitopes become associated with class II MHC when an antigen comprising the T epitope binds to the surface of an antigen presenting cell. The antigen enters the cell via phagocytosis or by receptor mediated endocytosis in clathrin coated vesicles. Alternatively, soluble antigens may be internalized by fluid phase pinocytosis. Once the antigen is internalized it is processed by cellular proteases in acidic vesicles resulting in peptides 10–20 amino acids long. These epitopes bind MHC class II molecules in intracellular vesicles and the complex is transported to the cell surface. The presence of the MHC class II-antigen complex on the surface of antigen presenting cells results in the stimulation of subpopulations of T helper cells. These cells aid CTL function as well as B cell responses. In addition, T helper cells can mediate inflammatory responses.

Two important factors in determining the character of an immune response are the nature of the antigen that is recognized and the intracellular or extracellular targeting of the antigen. Thus, a T cell epitope that can be targeted to enter an antigen presenting cell in a receptor mediated endocytosis dependent way will become associated with class II MHC and activate T helper cells but not CTL cells. Moreover, if a foreign T cell epitope can be directed to the cytoplasm of a target cell in a receptor mediated endocytosis independent fashion, the epitope will become associated with class I MHC and permit the activation of CTL cells. Therefore, there exists a need in the art to specifically target epitopes in order to selectively activate a cell mediated or humoral immune response.

SUMMARY OF THE INVENTION

This invention relates to a recombinant plasmid useful for expressing adenylate cyclase, wherein the plasmid comprises the cyaA and the cyaC genes of *Bordetella sp.* adenylate cyclase, or homologs thereof, operably linked to an expression control sequence, wherein the recombinant plasmid directs the expression of *Bordetella sp.* adenylate cyclase in a transformed host cell selected from the group consisting of bacteria, eukaryotic cells and yeast. In a specific embodiment of this invention, the cyaA gene and the cyaC gene are the cyaA gene and the cyaC gene of *Bordetella pertussis*. In other specific embodiments of this invention, the host cell is *E. coli*, the expression control sequence comprises the lac promoter, or the cyaA gene comprises DNA encoding a heterologous epitope. In one specific embodiment, the recombinant plasmid is pCACT3.

This invention also relates to a recombinant DNA molecule comprising the cyaA adenylate cyclase gene of *Bordetella sp.* or homologs thereof, wherein the cyaA gene contains at least one insertion of a heterologous DNA sequence at at least one permissive site. In embodiments of this invention the heterologous DNA sequence encodes less than 25 amino acids, between 10–20 amino acids and 16 amino acids. In specific embodiments of this invention the heterologous DNA sequence is an epitope of poliovirus, HIV virus, influenza virus, or lymphocytic choriomeningitis virus and is inserted in the N-terminal catalytic domain or the C-terminal domain.

This invention further relates to a recombinant *Bordetella pertussis* adenylate cyclase comprising a heterologous epitope at a permissive site. In one embodiment of this invention the adenylate cyclase is in detoxified form. In specific embodiments of this invention the heterologous epitope is inserted into the N-terminal catalytic domain and the heterologous epitope is presented to CD8⁺ T lymphocytes in association with molecules of class I major histocompatability complex. In other specific embodiments of this invention the heterologous epitope is inserted into the C-terminal domain and is presented to CD4⁺ T lymphocytes in association with molecules of class II major histocompatability complex.

In a specific embodiment of this invention the permissive site of the *Bordetella pertussis* adenylate cyclase is selected from the group consisting of residues 137–138, residues 224–225, residues 228–229, residues 235–236 and residues 317–318. In other specific embodiments of this invention the heterologous epitope of the recombinant *Bordetella pertussis* adenylate cyclase is epitope 118–132 of the nucleoprotein of the lymphocytic choriomeningitis virus, an epitope of HIV virus, in particular the epitope included in the V3 loop, an epitope of influenza virus, or an epitope of poliovirus, in particular epitope 103–116 of poliovirus.

Moreover, this invention relates to a method of inducing a B cell immune response comprising immunizing animals with live bacteria expressing a recombinant adenylate cyclase or an immunological composition comprising a recombinant adenylate cyclase or a fragment of AC, wherein the recombinant adenylate cyclase comprises a heterologous B epitope.

In specific embodiments of this invention, the bacteria used in the method of inducing a B cell immune response are *E. coli*. In a further embodiment, the animals immunized with the immunological composition or bacteria are humans. In specific embodiments, the heterologous B epitope is a poliovirus B epitope, an HIV B epitope, a lymphocytic choriomeningitis virus B epitope, or an influenza virus B epitope.

This invention also relates to a method of inducing a CD4⁺ T cell immune response, wherein the method comprises immunizing animals with an immunological composition comprising a recombinant adenylate cyclase, wherein said recombinant adenylate cyclase comprises a heterologous T epitope at a permissive site in the C-terminal domain of said recombinant adenylate cyclase.

In a specific embodiment of this invention, the immunological composition further comprises a suitable adjuvant. In a further embodiment, the heterologous T epitope is a T epitope of poliovirus, HIV, influenza virus, or lymphocytic choriomeningitis virus.

This invention further relates to a method of inducing CD8⁺ T cell immune response, wherein the method comprises immunizing animals with an immunological composition comprising a recombinant adenylate cyclase, wherein the recombinant adenylate cyclase comprises at least one heterologous CTL epitope at at least one permissive site in the N-terminal catalytic domain of the recombinant adenylate cyclase.

In a specific embodiment of this invention, the immunological composition further comprises a suitable adjuvant, such as aluminum hydroxide. In a further embodiment, the heterologous T epitope is a T epitope of poliovirus, HIV, choriomeningitis virus, particularly epitope 118–132 of the nucleoprotein of the choriomeningitis virus, or influenza virus.

BRIEF DESCRIPTION OF FIGURE

The FIGURE represents schematically a method of constructing plasmid pCACT3. The sequences depicted in this FIGURE are SEQ ID NO:6: (top sequence) and SEQ ID NO:7: (bottom sequence).

DETAILED DESCRIPTION OF THE PREFERRED EMBODIMENTS

As used herein, the term "expression control sequence" refers to a sequence of nucleic acid that regulates the transcription and/or translation of a structural gene. This regulation can be direct or indirect. Thus, examples of expression control sequences include promoters, operators, ribosome binding sites and DNA that encodes ribosome binding sites.

As used herein, the term "heterologous DNA sequence" refers to a DNA sequence derived from the DNA of a species other than the DNA of the remainder of the molecule or gene in which the heterologous sequence is located. The heterologous DNA sequence can be synthesized enzymatically or chemically. Alternatively, the heterologous DNA sequence may be directly isolated from a source organism.

As used herein with reference to a protein the term "permissive site" refers to a site within the protein molecule, where exogenous amino acids may be added without appreciably affecting the functional properties of the protein.

As used herein with reference to a nucleic acid, the term "permissive site" refers to a site within the nucleic acid, where exogenous nucleotides can be added while maintaining reading frame without appreciably affecting the functional properties of a protein expressed from the nucleic acid.

As used herein, the term "epitope" refers to a sequence of amino acids, or another molecule or fragment thereof, that can induce an immune response.

As used herein, the term "B epitope" refers to a sequence of amino acids, or another molecule or fragment thereof, that can induce an immune response involving B lymphocytes.

As used herein, the term "heterologous epitope" refers to an epitope that can be inserted in a protein by recombinant techniques wherein the inserted epitope is not naturally found in this protein.

*E. coli* strain XL-1 containing pCACT3 was deposited with the Collection Nationale de Cultures de Microorganisms of Institut Pasteur, 28 rue du Docteur Roux, 75724 Paris, Cedex 15, France under accession number I-1201 on Apr. 8, 1992.

The mechanisms by which the immunogenicity of defined peptide epitopes is controlled involves both the intrinsic characteristics of a given epitope and environmental factors. These environmental factors include whether the epitope is exposed as part of complex and organized structures such as parasites or bacteria. By expressing a given peptide epitope in different permissive sites of various bacterial proteins it is possible to alter the environmental factors and thus specifically modify the immunogenicity of the peptide epitope.

The adenylate cyclase of *Bordetella pertussis* represents a suitable vehicle to specify the immunogenic response of a heterologous peptide epitope in embodiments of this invention. The *Bordetella pertussis* adenylate cyclase constitutes one of the essential toxins of this organism which is the causative agent of whooping cough. The adenylate cyclase is secreted by *Bordetella pertussis* and possesses the ability to enter target eukaryotic cells where, activated by calmodulin (CAM), it catalyzes the synthesis of cyclic AMP (cAMP) thereby impairing cellular metabolism. The adenylate cyclase (AC) is synthesized and secreted in the form of a polypeptide of 1706 amino acids: the calmodulin-dependent catalytic activity is localized in the first 400 amino acids. The C-terminal portion of approximately 1300 residues is responsible for the binding to the target cells and for the translocation of the N-terminal catalytic domain through the cytoplasmic membrane of these cells. In addition, this C-terminal portion possesses a weak hemolytic activity.

Several features of *Bordetella pertussis* AC indicate that this toxin can be used as a vehicle for inducing a specific immunogenic response:

1) this adenylate cyclase is capable of entering many different cells, especially various types of cells associated with the immune system;
2) the adenylate cyclase may be internalized by the target cells independent of a receptor mediated endocytosis process suggesting that the catalytic domain of the toxin is capable of penetrating directly through the cytoplasmic membrane of the target cells;
3) the N-terminal catalytic domain undergoes rapid proteolysis inside the target cells allowing epitopes associated with this domain to enter the class I MHC pathway of antigen presentation; and
4) a number of amino acids involved in the catalytic activity of AC are identified, permitting the construction of modified AC toxins that are devoid of enzymatic activity and hence are no longer cytotoxic. See Sakamoto, H., Sebo, P., Ladant., J. Biol. Chem., 267:13598-13602 (1992).

The *Bordetella pertussis* adenylate cyclase (Cya) toxin-encoding genetic locus (cya) is composed of five genes (cyaA-E). The cyaA gene encodes the adenylate cyclase. Expression of the cyaA gene in *E. coli* leads to the production of a 200 kDa gene product exhibiting catalytic activity, but devoid of invasive and hemolytic activities. However, the coexpression of the cyaC gene product renders the cyaA holotoxin invasive and hemolytic in a reconstituted expression system in *E. coli*. Coexpression of the cyaB, D, and E genes in trans to cyaA does not confer invasiveness and hemolytic activity upon the holotoxin, nor does it potentiate the activities brought about by the cyaC gene product.

It is believed that CyaC-mediated activation of CyaA results from a post-translational modification. This modification is not lost during toxin purification from *B. pertussis* by a procedure including 8M urea extraction or SDS-PAGE separation (Hewlett et al., 1989). This finding indicates that the modification is covalent.

The invasive and hemolytic activities of CyaA toxins produced recombinantly in *E. coli* or naturally in *B. pertussis* were compared. The results indicate that the CyaC-activated proteins produced in *E. coli* show 5 times lower hemolytic activity than the toxin produced in *B. pertussis*. The ratio of hemolytic vs. invasive activity did not change significantly with the purification of the proteins, indicating that the decreased hemolytic activity is not due to some inhibitory factor present in *E. coli* extracts, but rather reflects an intrinsic property of the toxins produced in *E. coli*. Two additional arguments support this interpretation. First, the time course of hemolysis is almost linear, regardless of the source of the toxins indicating that the stabilities of the proteins purified from *E. coli* and *B. pertussis* are similar. Second, possible differences in the initial conformation of the toxins produced in the two organisms can be ruled out as the purification procedures involve complete denaturation in 8M urea.

This data indicates that the invasive and hemolytic activities of CyaA toxin can be separated. This suggests that distinct structural determinants within the CyaA toxin are involved in invasive and hemolytic activities. The decreased hemolytic activity of the toxin produced in *E. coli* could also be accounted for by a difference in the nature of the post-translational modifications taking place in the two organisms or by the presence of an additional factor present in *B. pertussis* that is necessary to confer full hemolytic activity to the toxin.

Expression vectors were constructed directing the expression of both the cyaA gene and the cyaC gene (Sebo et al., 1991). Additionally, another plasmid expression vector, pCACT3, was constructed which contains both the cyaA and cyaC genes. This expression vector permits a second compatible plasmid carrying genes necessary for the secretion of the cytotoxic AC in *E. coli*, such as hlyB and hlyD as described in Meckman et al., 1985.

Plasmid pCACT3 was constructed in several steps (See FIG. 1):

1) plasmid pAHL1 was constructed by inserting between the single PstI and EcoRI sites of plasmid pACM384, the oligonucleotide 5'CTG CAGG TCG ACT CTA GAG GAT CCC CGG GTA CCT AAG TAAC TAA GAA TTC3' (SEQ ID NO:1);

2) The 1.4-kb PvuII-EcoRI fragment of pAHL1 was subcloned into the multiple cloning site of phagemid pTZ19R (Pharmacia) between the PstI site (converted to a blunt end with T4 polymerase) and EcoRI site. The resulting plasmid is pACDL21;

3) A 5.4-kb BclI-ScaI fragment originating from plasmid pACT7 (Sebo et al., 1991) was inserted between the single BclI-ScaI sites of pACDL21 to give plasmid pDLACT1;

4) A 0.636-kb NaeI-DdeI fragment of plasmid pDIA4 (Glaser et al., 1988) containing the cyaC gene was subcloned into the SmaI site of the vector pTZ18R (Pharmacia) to give plasmid pCYACI in which the cyaC gene is under the control of the promoter;

5) The HindIII-ScaI fragment of pDLACT1 containing the cyaA gene (6.2 kb) was subcloned between the HindIII and ScaI sites of pCYAC1 to give plasmid pCACT3.

Thus, the AC toxin may be expressed in *E. coli* and/or secreted by this bacterium in large amounts, and it is readily purified (affinity chromatography on CaM Affi-Gel resin).

We have developed a methodology which makes it possible to identify readily, using a double selection (resistance to an antibiotic and calorimetric test on dishes by α-complementation), oligonucleotide insertions (which preserve the reading frame) in the portion of the gene coding for the N-terminal catalytic domain of the toxin. The functional consequences of these mutations on the catalytic activity of the toxin may be readily analyzed, both genetically (functional complementation of an *E. coli* cya⁻ strain) and biochemically (characterization of the stability of the modified ACs, of their enzymatic activity, of their interaction with CaM, etc.). This methodology has enabled a large number of mutations to be screened in order to identify the sites which are potentially advantageous for the insertion of antigenic determinants. The plasmids which were used for this identification were derivatives of pDIA5240 (P. Sebo, P. Glaser, H. Sakamoto and A. Ullman, *Gene* 1991, 104, 19–24, the contents of which are hereby incorporated by reference) containing the first 459 codons of the cyaA gene and which expressed the N-terminal portion of the AC (399 amino acids), devoid of all invasive or cytotoxic activity.

Specifically, a PvuII-Bst fragment of pDIA5240 comprising 373 bp codons of CyaA was ligated to the 3' terminal portion of the gene (3999 base pairs—1333 codons). The resulting protein thereby regains, in the presence of the product of the cyaC gene, its invasive power. Additional peptide sequences of 10 to 20 amino acids were then inserted at the previously identified sites in order to analyze the cytotoxicity of the recombinant toxins. In specific embodiments of this invention this insertion is at restriction sites of the cyaA gene. The modified toxins which retain their cytotoxicity (that is to say whose N-terminal catalytic domain is normally transported into the cytoplasm of the target cells) may be used as a vehicle for presentation of antigenic determinants. See Ladant et al., 1992, the contents of which are hereby incorporated by reference. We have defined in this manner five permissive sites in the N-terminal portion of the AC (insertion between amino acids 137–138, 224–225, 228–229, 235–236 and 317–318). A more exhaustive mapping will enable the person of ordinary skill in the art to locate other permissive sites using the methods described herein.

We have developed a second methodology (resistance to an antibiotic and hemolysis test on Petri dishes containing blood) which enables in-frame oligonucleotide insertions in the portion of the gene coding for the hemolytic C-terminal portion of the toxin to be identified. These insertions are carried out on a plasmid which permits coexpression of both cyaA and cyaC genes, such as pCACT3. See supra. The advantage of characterizing "permissive" sites for the insertion of additional peptide sequences in the carboxy-terminal portion of the toxin lies in the fact that, in contrast to the N-terminal domain, this domain remains associated with the outer surface of the cytoplasmic membrane. Thus, epitopes inserted into this region of the toxin might be directed towards the pathway of antigenic presentation specific to class II MHC. Thus, toxins can be constructed that are doubly modified—in the N-terminal catalytic domain and in the C-terminal domain—and capable of possessing both epitopes directed to class I MHC and other epitopes directed to class II MHC.

A/ RECOMBINANT ADENYLATE CYCLASES EXPRESSING HETEROLOGOUS EPITOPES: VACCINE APPLICATIONS

1. Insertion of B or T epitopes.

*B. pertussis* AC toxin is used to present epitopes of vaccinal importance to the immune system. This recombinant toxin may be used as a component of the vaccine, either alone or in the presence of other antigenic preparation(s). It can be used in toxic form or in detoxified form. The detoxified form can be obtained by directed mutagenesis. For example, by replacing Lys58 or Lys65 (Glaser et al., 1989, the contents of which are hereby incorporated by reference) by a Gln residue. Alternatively, the detoxified form may be obtained by inserting the oligonucleotide CTG CAG at the EcoRV site at position 564 of the coding phase of the cyaA gene. See Ladant et al., 1992.

DNA encoding *B. pertussis* adenylate cyclase derivative of the invention can be obtained, by way of example, as follows.

Plasmid pDIA5240 is linearized at a restriction site where DNA encoding a heterologous epitope is to be inserted. In specific embodiments of this invention, the restriction site is NruI when the permissive site is at residues 137–138 or at residues 235–236. In other embodiments the restriction site is HindIII when the permissive site is at residues 224–225, at residues 228–229, or at residues 317–318. The resulting pDIA5240 derivative containing heterologous epitope(s) at a permissive site is restricted with PvuII and BstBL A 1.4 Kb fragment is isolated containing the portion of the adenylate cyclase gene coding for the N-terminal catalytic domain and comprising a heterologous epitope. The restriction fragment is then fused to the remainder of cyaA gene by inserting it between the HindIII site (connected to a blunt-end by T4 DNA polymerase) and BstBI site of pCACT3. The heterologous epitope can be inserted into pDIA5240 as a part of a linker that is compatible with an appropriate permissive site. In specific embodiments of this invention the linker codes for about 16 amino acids.

Any epitope recognized by the cells of the immune system, B or T lymphocytes, may be introduced into the permissive sites of the AC. Each molecule of toxin may comprise one or more copies of the same epitope, or a combination of different epitopes, B or T located in various sites of the toxin.

1.1 B epitopes:

Any epitope recognized by B lymphocytes and capable of inducing antibodies possessing biological activity may be introduced into the toxin. Thus, for example, the C3 epitope of the polio virus or the V3 epitope of the HIV virus, which are capable of inducing antibodies neutralizing these viruses, will be introduced into the toxin. In a preferred embodiment of this invention, the V3 epitope of the HIV virus to be inserted is RIQRGPGRAFVTIGK (residues 315–329) (SEQ ID NO:2). In the case of the V3 epitope, V3 epitopes corresponding to the various isolates of the virus may be introduced into various sites of the toxin.

Similarly, recombinant toxins possessing other epitopes of the HIV virus (and in particular conserved epitopes) can be prepared. Each molecule of toxin may hence present different B epitopes, in the presence or absence of other epitopes (and in particular of T epitopes). The vaccinal preparations may comprise molecules of recombinant toxin possessing different epitopes.

Immunization with the molecules of recombinant toxins and detection of antibodies is carried out as described in Leclerc et al., 1991, which is hereby incorporated by reference.

1.2 Helper T epitopes (CD4+):

The molecules of recombinant toxin may also be used to present epitopes recognized by CD4+ T lymphocytes. These epitopes will be inserted either alone or in combination with other T or B epitopes. There may thus be inserted the T epitopes 103–116 of the poliovirus, alone or in continuity with the B epitope 93–103, T epitopes of the HIV virus, and in particular the T epitope included in the V3 loop, or the T epitope of the lymphocytic choriomeningitis virus included in the region 118–132 of the nucleoprotein. The sequence of region 118–132 of the nucleoprotein of lymphocytic choriomeningitis virus is RPQASGVYMGNLTAQ (SEQ ID NO:3).

The sequence of the B epitope 93–103 of poliovirus (C3 epitope) is:

DNPASTTNKDK (SEQ ID NO:4)

The sequence of the T epitope is:

KLFAVWKITYKDT. (SEQ ID NO:5)

For the generation of helper CD4+ T responses, the T epitopes will preferably be inserted into the C-terminal region of the toxin capable of entering the presenter cell by an endocytosis pathway. Toxin molecules possessing AC activity or mutated to lose this activity may be used, depending on the type of CD4+ response desired. The recombinant molecule can consist of a fragment or the complete adenylate cyclase protein expressing foreign epitope(s).

1.3 The detection of CD4+ responses after immunization with adenylate cyclase molecules presenting one or more T epitopes recognized by CD4+ lymphocytes:

Animals, such as mice of different strains, are immunized with the molecules of recombinant toxin in the presence of suitable adjuvant, such as Freunds' complete adjuvant, Freunds' incomplete adjuvant, or aluminum hydroxide. Two weeks later, the CD4+ T responses are determined by proliferation of lymphocytes (spleen or draining lymph nodes), cultured with the peptide corresponding to the inserted T epitope as described previously. See Fayolle, et al., 1991. Conversely, the recognition by lymphocytes of mice immunized with peptides of molecules of recombinant toxin in vitro is determined by incorporation of thymidine. See Leclerc, et al. 1991.

1.4 Insertion of T epitopes recognized by cytotoxic T lymphocytes:

AC toxin possesses the ability to enter the cytoplasm of target cells. This makes it possible to deliver T epitopes recognized by CD8+ T lymphocytes to the cytoplasm of these cells, and to permit association of these epitopes with molecules of the class I MHC. Sources of AC are *Bordetella sp.* or other organisms expressing AC. In embodiments of this invention, the adenylate cyclase is a calmodulin dependent AC. In specific embodiments, the AC is *Bordetella pertussis* AC.

1.5 Induction of cytotoxic T cells:

Cytotoxic T responses can be obtained by immunization with the recombinant toxin, alone or in the presence of an adjuvant such as aluminum hydroxide. The routes can be the oral route, the subcutaneous or the intramuscular route.

The recombinant toxin expresses one or more epitopes recognized by cytotoxic T cells. Other epitopes, in particular epitopes recognized by CD4+ helper T lymphocytes, can be inserted into the same molecule of toxin. The identification of an epitope as a CTL epitope or a T helper epitope is determined experimentally.

As an example, we have inserted into the toxin the epitope 118–132 of the nucleoprotein of the lymphocytic choriomeningitis virus (Aichele, et al. 1990), which is both a CTL and a T helper epitope. The amino acid sequence of this epitope is: RPQASGVYMGNLTAQ (SEQ ID NO:3). Epitopes of other pathogens and in particular of HIV, can be inserted (CTL epitopes of the env, gag, nef proteins, etc.). Examples of suitable epitopes are described by Nixon et al., 1992, which is expressly incorporated herein by reference. Several epitopes representing the sequences of various isolates of the HIV virus can be introduced into the same molecule of toxin. Similarly, it is possible to use a mixture of molecules of recombinant toxin, each presenting a CTL epitope corresponding to a given isolate of the HIV virus.

1.6 Detection of cytotoxic T responses:

Lymphocytes obtained from animals immunized with the recombinant toxin are stimulated for 5 days with syngeneic cells coated with the peptide corresponding to the inserted epitope, or in the presence of the recombinant toxin. The detection of cytotoxic T effectors is carried out as described previously (Fayolle et al., 1991. The target cells, labeled with chromium-51 ([$^{51}$Cr]) and possessing the class I molecules compatible with the effector cells, are incubated beforehand with the peptide corresponding to the CTL epitope inserted into the recombinant toxin. The cytotoxic T response is estimated by release of [$^{51}$Cr] by the lysed target cells.

B/ RECOMBINANT ADENYLATE CYCLASES EXPRESSING HETEROLOGOUS EPITOPES OR A LIGAND FOR A GIVEN RECEPTOR: IMMUNOTOXIN APPLICATIONS

The recombinant AC toxin can be used to target cell antigens and receptors. Following are examples of several constructions may be envisaged:

1) construction of fusion proteins containing the first 1490 amino acids of the AC (this truncated form of the toxin is incapable of binding to the target cells and is hence not toxic), fused with a growth factor such as TGF-α (in which the target is the EGF receptor), with IL-2, IL-4 or IL-6 or any other lymphokine, with variable regions of antibodies having a strong affinity with receptors or antigens to be targeted, for example tumor antigens;

2) insertion of B epitopes into the AC for targeting of specific B cells, or insertion of any other peptide ligand recognizing specific receptors;

3) construction of an AC carrying an additional cysteine at the C-terminal end of the protein, which will enable a specific polypeptide to be fused to the AC by chemical coupling. It should be recalled that the AC is a protein which does not contain cysteine.

The potential importance of B. pertussis AC toxin compared to other immunotoxins lies in the fact that the poisoning of the target cells by the AC is independent of a receptor mediated endocytosis process. Thus, any surface marker specific to a given cell could serve as a receptor for targeting the recombinant AC toxin comprising a truncated AC toxin fused with a specific ligand.

REFERENCES

Aichele, P., H. Hengartner, R. M. Zinkernagel and M. Schultz (1990), J. Exp. Med., 171, 1815–1820.

Barany, F. (1985a) Proc. Natl. Acad. Sci. U.S.A. 82, 4202–4206.

Barany, F. (1985b) Gene (Amst.) 37, 111–123.

Charbit, A., Ronco, J. Michel, V., Werts, C. and Hofnung, M. (1991) J. Bacteriol. 173, 262–275.

Fayolle, C., Deriaud, E., Leclerc, C. (1991) J. Immunol. 147, 4069–4073.

Freimuth, P. I. and Ginsberg, H. S. (1986) Proc. Natl. Acad. Sci. U.S.A 83, 7816–7820.

Freimuth, P. I., Taylor, J. W., and Kaiser E. T. (1990) J. Biol. Chem. 265, 896–901.

Glaser, P., Ladant, D., Sezer, O., Pichot, F., Ullmann, A., and Danchin, A. (1988) Microbiol. 2, 19–30.

Glaser, P., Ladant, D., Sezer, O., Pichot, F., Ullmann, A., and Danchin, A. (1989) EMBO J. 8, 967–972.

Glaser, P., Munier, H. Gilles, A. M. Krin, E., Porumb, T., Barzu, O., Sarfati, R., Pellecuer, C., and Danchin, A. (1991) EMBO J 10, 1683–1688.

Hewlett, E. L., Gordon, V. M., McCaffery, J. D., Sutherland, W. M., and Gray, M. C. (1989) J. Biol. Chem. 264, 19379–19384.

Kumar, G. B., and Black, P. N. (1991) J. Biol. Chem. 266, 1348–1353.

Ladant, D., Glaser, P., Ullmann, A. (1992) J. Biol. Chem. 267, 2244–2250.

Leclerc, C., Charbit, A., Martineau, P., Deriaud, E., Hofnung, M. (1991) J. Immunol. 147, 3545–3552.

Meckman, N., Nicaud, J. H., Gray, L. and Holland, I. B. (1985) Mol. Gen. Genet. 201, 282–288.

Nixon, D. F., Broliden, V., Ogg, G. and Biolider, P. A. (1992), Immunology, 76:515–534.

Sebo, P., Glaser, P., Sakamoto, H., and Ullmann, A. (1991) Gene (Amst.) 104, 19–24.

Starzyk, R. M., Burbaum, J. J., and Schimmel, P. (1989) Biochemistry 28, 8479–8484.

---

What is claimed is:

1. A recombinant DNA molecule comprising an adenylate cyclase gene of Bordetella, wherein said adenylate cyclase gene contains a heterologous DNA sequence encoding at least one heterologous epitope at DNA encoding residues 235–236 of the gene product of said adenylate cyclase gene.

2. The recombinant DNA molecule as claimed in claim 1, wherein said heterologous DNA sequence encodes the C3 epitope of human poliovirus.

3. The recombinant DNA molecule as claimed in claim 1, wherein said heterologous DNA sequence encodes an epitope of HIV virus.

4. The recombinant DNA molecule as claimed in claim 3, wherein said epitope is the V3 epitope of HIV virus.

5. The recombinant DNA molecule as claimed in claim 1, wherein said heterologous DNA sequence encodes residues 118–132 of the nucleoprotein of lymphocytic choriomeningitis virus.

6. A recombinant DNA molecule comprising an adenylate cyclase gene of *Bordetella pertussis*, wherein said adenylate cyclase gene contains a heterologous DNA sequence encoding at least one heterologous epitope at DNA encoding residues 235–236 of the gene product of said adenylate cyclase gene.

7. The recombinant DNA molecule as claimed in claim 6, wherein said heterologous DNA sequence encodes the C3 epitope of human poliovirus.

8. The recombinant DNA molecule as claimed in claim 6, wherein said heterologous DNA sequence encodes an epitope of HIV virus.

9. The recombinant DNA molecule as claimed in claim 8, wherein said epitope is the V3 epitope of HIV virus.

10. The recombinant DNA molecule as claimed in claim 6, wherein said heterologous DNA sequence encodes residues 118–132 of the nucleoprotein of lymphocytic choriomeningitis virus.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CTGCAGGTCG ACTCTAGAGG ATCCCCGGGT ACCTAAGTAA CTAAGAATTC          50
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Arg  Ile  Gln  Arg  Gly  Pro  Gly  Arg  Ala  Phe  Val  Thr  Ile  Gly  Lys
 1              5                        10                       15
```

( 2 ) INFORMATION FOR SEQ ID NO:3:

( i ) SEQUENCE CHARACTERISTICS:
        ( A ) LENGTH: 15 amino acids
        ( B ) TYPE: amino acid -continued (D) TOPOLOGY: linear (ii) MOLECULE TYPE: peptide (xi) SEQUENCE DESCRIPTION: SEQ ID NO:3:

```
Arg Pro Gln Ala Ser Gly Val Tyr Met Gly Asn Leu Thr Ala Gln
1               5                   10                  15
```

(2) INFORMATION FOR SEQ ID NO:4:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:4:

```
Asp Asn Pro Ala Ser Thr Thr Asn Lys Asp Lys
1               5                   10
```

(2) INFORMATION FOR SEQ ID NO:5:

(i) SEQUENCE CHARACTERISTICS:
(A) LENGTH: 13 amino acids
(B) TYPE: amino acid
(D) TOPOLOGY: linear (ii) MOLECULE TYPE: peptide (xi) SEQUENCE DESCRIPTION: SEQ ID NO:5:

```
Lys Leu Phe Ala Val Trp Lys Ile Thr Tyr Lys Asp Thr
1               5                   10
```

(2) INFORMATION FOR SEQ ID NO:6:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

```
GGTCGACTCT AGAGGATCCC CGGGTACCTA AGTAACTAAG                                40
```

(2) INFORMATION FOR SEQ ID NO:7:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

```
AATTCTTAGT TACTTAGGTA CCCGGGGATC CTCTAGAGTC GACCTGCA                       48
```